US00PP14599P29

(12) United States Plant Patent
Zaiger et al.

(10) Patent No.: US PP14,599 P2
(45) Date of Patent: Mar. 16, 2004

(54) INTERSPECIFIC TREE NAMED 'EMERALD GEM'

(50) Latin Name: ***Prunus salicina*×(*Prunus salicina*× *Prunus armenica*)×(*Prunus salicina*× *Prunus armeniaca*)**
Varietal Denomination: Emerald Gem

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 38 days.

(21) Appl. No.: 10/431,659

(22) Filed: May 9, 2003

(51) Int. Cl.[7] ..... A01H 5/00
(52) U.S. Cl. ..... Plt./180
(58) Field of Search ..... Plt./180

*Primary Examiner*—Anne Marie Grunberg

(57) ABSTRACT

A new and distinct variety of interspecific tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit with excellent flavor and eating quality.
2. Fruit having a high degree of soluble solids (average 20° Brix).
3. Mild, sweet fruit having a good balance between acid and sugar, with a flavor blend of plum and apricot.
4. Heavy and regular production of medium size fruit.
5. Vigorous, upright tree growth.
6. Fruit maintaining firmness on tree approximately 2 weeks after maturity (shipping ripe).
7. Relatively uniform size of fruit throughout the tree.

1 Drawing Sheet

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plum and interspecific trees, which are known to us, and mentioned herein, 'Friar' Plum (non-patented), 'Red Beaut' Plum (U.S. Plant Pat. No. 2,539) and 'Flavor Queen' Interspecific (U.S. Plant Pat. No 7,420).

STATEMENT REGARDING FEDERALLY SPONSORED RESEARCH AND DEVELOPMENT

Not applicable.

ORIGIN OF THE VARIETY

The present new and distinct variety of interspecific tree [*Prunus salicina*×(*Prunus salicina*×*Prunus armeniaca*)]× (*Prunus salicina*×*Prunus armeniaca*) was originated by us in our experimental orchard located near Modesto, Calif. as a first generation cross between two proprietary parents with the field identification numbers 29EB323 and 4G1180. The maternal parent (29EB323) originated from the cross of 'Friar' Plum (non-patented) with the proprietary plumcot (4G1180), which originated from a cross of 'Red Beaut' Plum (U.S. Plant Pat. No. 2,539) with an apricot of unknown parentage. The paternal parent, the plumcot (4G1180) was crossed back to (29EB323). A large number of these first generation seedlings growing on their own root system, were planted and maintained under close and careful observation, during which time the above new variety exhibited distinct and desirable fruit characteristics and was selected in 1987 for asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE VARIETY

A new and distinct variety of interspecific tree, which is of large size, vigorous, upright growth and a regular and productive bearer of medium size, yellow flesh, clingstone fruit. The fruit is further characterized by being relatively uniform in size throughout the tree, holding firm on the tree for approximately 2 weeks after maturity, having excellent flavor and eating quality with a blend between plum and apricot and having high soluble solids (average 20° Brix). The present variety of interspecific tree is similar to a plum tree except slightly more spreading in growth and has a slightly rougher bark on both limbs and trunk. In comparison to the fruit of the interspecific variety 'Flavor Queen' (U.S. Plant Pat. No. 7,420), the fruit is approximately 18 days earlier in maturity. In comparison to the 'Red Beaut' Plum (U.S. Plant Pat. No. 2,539), the new variety has heavier production with fruit that has yellow skin color compared to red, is higher in Brix with greater eating quality and is approximately 38 days later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color.

Tree:

*Size.*—Large. Pruned to 3 to 3.5 meters in height for economical harvesting of fruit.

*Vigor.*—Vigorous. Growth of 1.5 to 2 meters in height the first growing season. Varies with soil type, fertility and climatic conditions.

*Form.*—Upright, usually pruned to vase shape.

*Branching habit.*—Upright. Crotch angle approximately 30°, the weight of the fruit tends to increase the branch angle.

*Productivity.*—Heavy production. Thinning and spacing of fruit necessary to develop desired fruit size.

*Bearer.*—Regular. Three consecutive years of adequate fruit set. No alternate bearing observed.

*Fertility.*—Self sterile, pollenizer required.

*Density.*—Medium dense. Center branches removed to develop vase shape to increase sunlight and air movement throughout the tree to enhance fruit spur growth.

*Hardiness.*—Hardy in all stone fruit growing areas of California. Winter chilling requirement approximately 700 hours at or below 45° F.

Trunk:

*Size.*—Large. Average circumference of 48.3 cm at 35.6 cm above ground on a 6 year old tree.

*Stocky.*—Medium stocky.

*Texture.*—Medium shaggy, roughness increases with age.

*Color.*—Varies from 5Y 7/2 to 10YR 7/2. Varies with age of tree.

Branches:

*Size.*—Average circumference 18.5 cm at 1.2 meters above ground.

*Surface texture.*—Smooth on new growth, becoming medium rough on mature growth.

*Lenticels.*—Average of 42 in a 25.8 square cm section. Average length 3.6 mm. Average width 1.1 mm. Color varies from 5YR 5/8 1 to 5YR 5/10.

*Color.*—New growth 2.5R 4/8 where exposed to the sun, and 2.5GY 6/6 to 2.5GY 7/6 in the shade. Old growth 7.5R 5/2.

Leaves:

*Size.*—Medium. Average length 104.1 mm. Average width 33.1 mm.

*Form.*—Oblanceolate.

*Apex.*—Acuminate.

*Base.*—Cuneate.

*Margin.*—Serrate.

*Thickness.*—Medium.

*Surface texture.*—Upper surface relatively smooth, slight indentation over midrib and leaf veins, glabrous. Lower surface relatively smooth, small ridges created by midrib and pinnate venation, glabrous.

*Petiole.*—Average length 15.7 mm. Average width 1.2 mm. Grooved longitudinally. Color varies from 2.5GY 6/6 to 2.5YR 6/6.

*Glands.*—Globose. Small. Average length 1.0 mm. Average diameter 0.9 mm. Number varies from 1 to 3, average number 2. Located on the base of the leaf blade and the upper portion of the petiole. Color — upper edge 2.5R 3/8, lower portion 2.5GY 6/6.

*Color.*—Upper surface 5GY 4/4. Lower surface 5GY 5/4. Midrib color 2.5GY 8/6.

Flower buds:

*Size.*—Small. Average length 7.2 mm. Average diameter 3.3 mm.

*Hardiness.*—Hardy with respect to California winters.

*Form.*—Plump, conical, becoming slightly elongated before opening.

*Pedicel.*—Average length 6.6 mm. Average width 0.6 mm. Color varies from 5GY 6/6 to 5GY 7/6.

*Pubescence.*—Glabrous.

*Color.*—Mature N 9.5/, juvenile buds have very light pink near apex.

*Number of buds per spur.*—Varies from 2 to 12, average number 8.

Flowers:

*Size.*—Small. Average height 9.7 mm. Average diameter 14.5 mm.

*Petals.*—Number 5, alternately arranged to sepals. Ovate shape. Average length 5.2 mm. Average width 4.4 mm. Color N 9.5/. Margin — entire, some petals slightly scalloped.

*Sepals.*—Number 5, alternately arranged to petals. Triangular shape, both upper and lower surfaces glabrous. Average length 2.7 mm. Average width 1.6 mm. Color — upper surface 5GY 8/10. Lower surface 5Y 6/8.

*Stamens.*—Average number 20. Average filament length 7.7 mm. Filament color N 9.5/. Color of anthers 7.5YR 6/12.

*Pollen.*—Present, abundant. Self sterile, pollenizer required. Color — 2.5Y 7/12.

*Pistil.*—Normally 1, varies from 1 to 2. Average length 6.8 mm, stigma approximately 1.8 mm lower than the anthers. Color 2.5GY 9/2. Glabrous.

*Fragrance.*—Slight.

*Blooming period.*—Date of First Bloom Feb. 16, 2001. Date of Petal Fall Feb. 28, 2001. Varies slightly with climatic conditions.

*Color.*—N 9.5/.

*Number flowers per flower bud.*—Varies from 1 to 3, average of 2.

*Pedicel.*—Average length 7.2 mm. Average width 0.9 mm. Color 5GY 8/6.

Fruit:

*Maturity when described.*—Firm ripe.

*Date of first picking.*—Jul. 1, 2001.

*Date of last picking.*—Jul. 8, 2001. Varies slightly with climatic conditions.

*Size.*—Medium. Average diameter axially 53.9 mm. Average transversely in suture plane 60.3 mm. Average weight 101.7 grams, varies slightly with fertility of soil, amount of thinning and climatic conditions.

*Form.*—Nearly globose, slightly flattened at base and apex.

*Suture.*—Shallow, extends from base to apex.

*Ventral surface.*—Nearly rounded, only slightly lipped.

*Apex.*—Slightly retuse.

*Base.*—Retuse.

*Cavity.*—Rounded to slightly elongated in suture plane. Average depth 7.9 mm. Average diameter 9.5 mm.

Stem:

*Size.*—Medium. Average length 12.7 mm. Average diameter 1.6 mm.

*Color.*—Varies from 2.5GY 6/6 to 2.5GY 6/8.

Flesh:

*Ripens.*—Evenly.

*Texture.*—Firm, meaty.

*Fibers.*—Few, very small, tender.

*Firmness.*—Good, comparable to 'Friar' Plum (non-patented).

*Aroma.*—Very slight.

*Amydgalin.*—Undetected.

*Eating quality.*—Excellent.

*Flavor.*—Excellent, good balance between acid and sugar.

*Juice.*—Moderate amount, enhances flavor.

*Brix.*—Average 20°, varies slightly with amount of fruit per tree and climatic conditions.

*Color.*—Varies from 10YR 8/8 to 10YR 8/12. Pit cavity varies from 2.5Y 7/8 to 2.5Y 7/10.

Skin:

*Thickness.*—Medium.

*Surface.*—Smooth.

*Bloom.*—Light to moderate amount.

*Tendency to crack.*—Very slight.

*Color.*—Varies from 5Y 8/8 to 5Y 7/8. Slight speckling on skin surface resembling small lenticels. Sweetness and eating quality is good before skin color matures from green to yellow.

*Tenacity.*—Tenacious to the flesh.

*Astringency.*—None.

Stone:

*Type.*—Clingstone.

*Size.*—Small. Average length 19.0 mm. Average width 15.8 mm. Average thickness 11.1 mm.

*Form.*—Obovoid.

*Base.*—Straight.

*Apex.*—Cuspidate, short in length.

*Surface.*—Slightly pitted throughout. Short, shallow furrows running from base toward apex, except for two long grooves on each side of suture plane.

*Sides.*—Unequal. One side of stone extends further from center axis.

*Ridges.*—Small and narrow, extending from base toward apex.

*Tendency to split.*—None.

*Color.*—Varies from 10YR 5/6 to 10YR 7/6 when dry.

Kernal:

*Form.*—Oblong.

*Taste.*—Bitter, heavy amydgalin.

*Viability.*—Viable. Good embryo development.

*Size.*—Medium. Average length 14.9 mm. Average width 8.7 mm. Average breadth 5.3 mm.

*Skin color.*—10YR 6/8 when dry.

Use:

*Dessert.*—Market — local and long distance.

Keeping quality: Good, held firm for 3 weeks in cold storage at 38° to 42° F. with no internal break down or wooliness of flesh.

Shipping quality: Good, showed minimal bruising or skin scarring in picking, packing or shipping trials.

Plant/fruit disease resistance/susceptibility: No specific testing for relative plant/fruit disease has been designed. Under close observation during planting, growing and harvesting of fruit, under normal cultural and growing conditions near Modesto, Calif., no particular plant/fruit disease resistance or susceptibility has been observed. Any variety or selection observed during indexing of plant characteristics with abnormal susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of interspecific tree, substantially as illustrated and described, characterized by its large size, vigorous, upright growth and being a productive and regular bearer of medium size, yellow flesh, clingstone fruit with excellent flavor and eating quality; the fruit is further characterized by maintaining firmness on the tree for approximately 2 weeks after maturity, having high soluble solids, averaging 20° Brix and, in comparison to the interspecific fruit of 'Flavor Queen' (U.S. Plant Pat. No. 7,420), the fruit is approximately 18 days earlier in maturity.

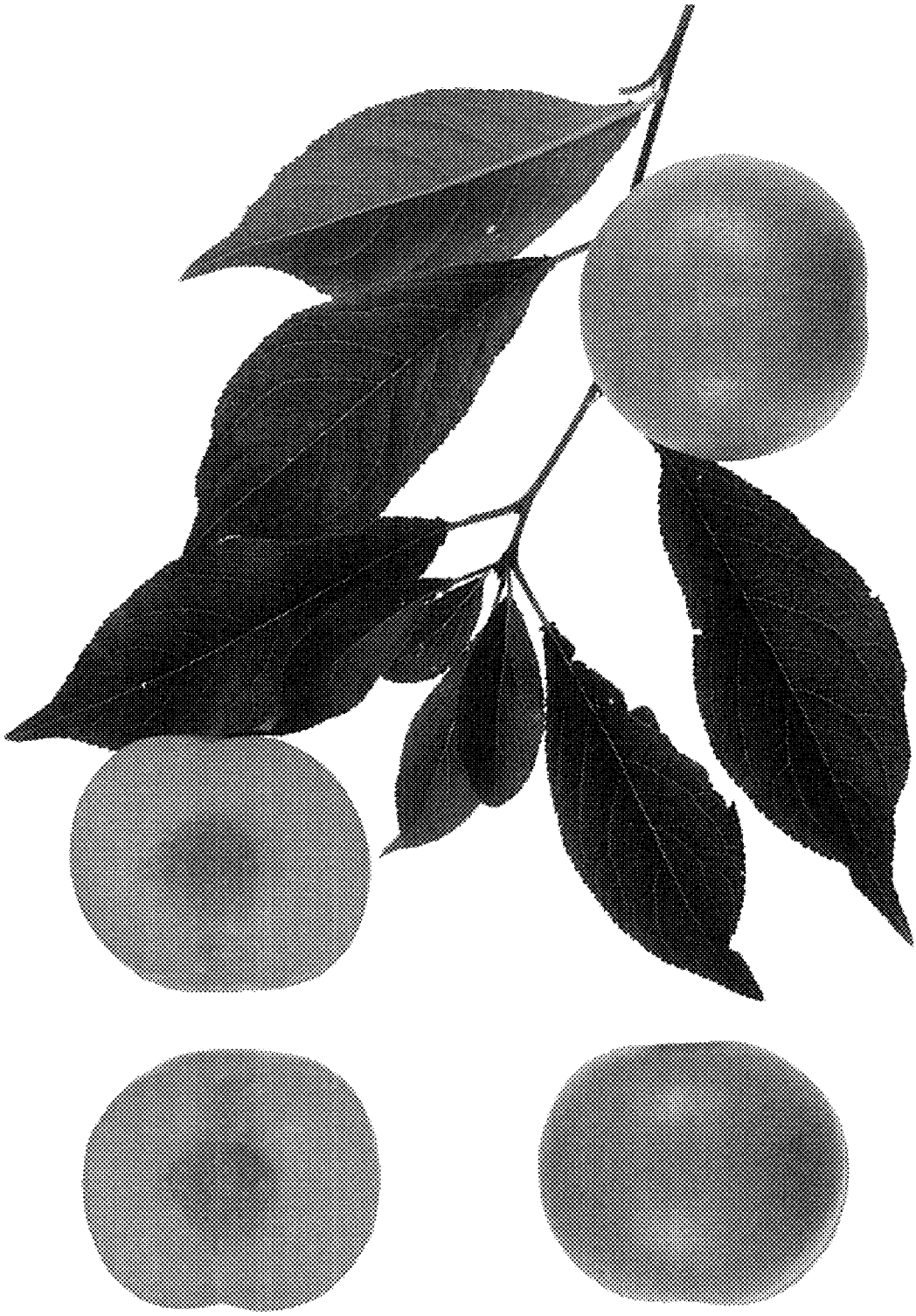

* * * * *